United States Patent
Seeley et al.

(10) Patent No.: US 9,172,192 B2
(45) Date of Patent: *Oct. 27, 2015

(54) IMPLANTABLE MEDICAL DEVICE HEADERS THAT FACILITATE DEVICE AND LEAD CONFIGURATION VARIANTS

(71) Applicant: Medtronic, Inc., Minneapolis, MN (US)

(72) Inventors: Dale F. Seeley, Spring Park, MN (US); Michael T. Hegland, Mounds View, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 106 days.

This patent is subject to a terminal disclaimer.

(21) Appl. No.: 14/016,395

(22) Filed: Sep. 3, 2013

(65) Prior Publication Data
US 2014/0099833 A1   Apr. 10, 2014

Related U.S. Application Data

(63) Continuation of application No. 13/598,606, filed on Aug. 29, 2012, now Pat. No. 8,523,617, which is a continuation of application No. 13/294,349, filed on Nov. 11, 2011, now Pat. No. 8,262,418, which is a continuation of application No. 12/891,984, filed on Sep. 28, 2010, now Pat. No. 8,075,346.

(60) Provisional application No. 61/256,537, filed on Oct. 30, 2009.

(51) Int. Cl.
| H01R 24/00 | (2011.01) |
| A61N 1/375 | (2006.01) |
| H01R 13/514 | (2006.01) |
| H01R 24/58 | (2011.01) |
| H01R 24/86 | (2011.01) |
| H05K 3/40 | (2006.01) |

(Continued)

(52) U.S. Cl.
CPC .............. *H01R 24/00* (2013.01); *A61N 1/3752* (2013.01); *H01R 13/514* (2013.01); *H01R 24/58* (2013.01); *H01R 24/86* (2013.01); *H05K 3/4038* (2013.01); *H01R 13/5224* (2013.01); *H01R 2107/00* (2013.01); *H01R 2201/12* (2013.01); *Y10T 29/49165* (2015.01)

(58) Field of Classification Search
CPC ............... H01R 24/58; H01R 2103/00; H01R 2107/00; H01R 2105/00; H04Q 1/142
USPC ......................................................... 439/668
See application file for complete search history.

(56) References Cited

U.S. PATENT DOCUMENTS

| 4,041,956 A | * | 8/1977 | Purdy et al. ..................... 607/36 |
| 4,182,345 A | * | 1/1980 | Grose .............................. 607/37 |

(Continued)

*Primary Examiner* — Abdullah Riyami
*Assistant Examiner* — Vladimir Imas
(74) *Attorney, Agent, or Firm* — Withers & Keys, LLC

(57) ABSTRACT

Implantable medical devices include headers having various features such as a modular design whereby the header is constructed from a series of stacked contact modules. Additional features include a feedthrough where pins exiting a housing of the implantable medical device extend into the header to make direct electrical connection to electrical contacts present within the header where those electrical contacts directly engage electrical connectors of leads inserted into the header. Other features include electrical contacts that are relatively thin conductors on the order of 0.040 inches or less and may include radial protrusions where the radial protrusions establish contact with the electrical connectors of the lead. Furthermore, electrical contacts may be mounted within the header in a floating manner so that radial movement of the electrical contact may occur during lead insertion.

16 Claims, 10 Drawing Sheets

(51) Int. Cl.
  *H01R 13/52* (2006.01)
  *H01R 107/00* (2006.01)

(56) References Cited

U.S. PATENT DOCUMENTS

| | | | | |
|---|---|---|---|---|
| 5,207,218 | A * | 5/1993 | Carpentier et al. | 607/36 |
| 5,692,926 | A * | 12/1997 | Jarl | 439/668 |
| 5,919,215 | A * | 7/1999 | Wiklund et al. | 607/36 |
| 6,574,508 | B2 * | 6/2003 | Zaouali et al. | 607/36 |
| 6,878,013 | B1 * | 4/2005 | Behan | 439/668 |
| 6,921,295 | B2 * | 7/2005 | Sommer et al. | 439/668 |
| 7,003,356 | B2 * | 2/2006 | Tsukamoto et al. | 607/57 |
| 7,069,081 | B2 * | 6/2006 | Biggs et al. | 607/37 |
| 7,070,455 | B2 * | 7/2006 | Balsells | 439/668 |
| 7,083,474 | B1 * | 8/2006 | Fleck et al. | 439/668 |
| 7,486,048 | B2 * | 2/2009 | Tsukamoto et al. | 320/112 |
| 7,647,110 | B2 * | 1/2010 | Hornfeldt et al. | 607/36 |
| 7,751,893 | B2 * | 7/2010 | Biggs et al. | 607/36 |
| 7,774,145 | B2 * | 8/2010 | Brauker et al. | 702/19 |
| 7,783,333 | B2 * | 8/2010 | Brister et al. | 600/345 |
| 7,905,833 | B2 * | 3/2011 | Brister et al. | 600/309 |
| 7,946,984 | B2 * | 5/2011 | Brister et al. | 600/365 |
| 7,949,381 | B2 * | 5/2011 | Brister et al. | 600/345 |
| 8,075,346 | B2 * | 12/2011 | Seeley et al. | 439/668 |
| 8,262,418 | B2 * | 9/2012 | Seeley et al. | 439/668 |
| 2007/0178770 | A1 * | 8/2007 | Rentas Torres | 439/668 |

* cited by examiner

IMPLANTABLE MEDICAL DEVICE HEADERS THAT FACILITATE DEVICE AND LEAD CONFIGURATION VARIANTS

RELATED APPLICATIONS

The present application claims priority to U.S. Provisional Application 61/256,537, entitled IMPLANTABLE MEDICAL DEVICE HEADERS THAT FACILITATE DEVICE AND LEAD CONFIGURATION VARIANTS, filed on Oct. 30, 2009, which is incorporated by reference herein.

TECHNICAL FIELD

Embodiments relate to implantable medical devices. More particularly, embodiments relate to implantable medical device headers that facilitate connector configuration variants of leads and devices.

BACKGROUND

Implantable medical devices (IMD) such as cardiac and neural stimulators utilize circuitry within an enclosure to generate electrical stimulation pulses. The circuitry is electrically linked to contacts within a header that is attached to the enclosure by a set of conductive pins known as a feedthrough. The implantable medical leads are physically connected to the header and include connectors on a proximal end that engage the electrical connectors within the header. The implantable medical leads also include electrodes near a distal end with the conductors carrying the stimulation pulses from the connectors to the electrodes.

The number of leads needed for a particular therapy and corresponding IMD may vary as may the number of electrical connections per lead. Hence the design of the header must also vary to accommodate the feedthrough of a given device and the number of leads and lead connectors that are necessary. For example, 24 electrodes may be configured in numerous ways for a device and therapy. One neurostimulator may drive eight electrodes per lead for three leads. Another neurostimulator may drive eight electrodes per lead for two leads and four electrodes per lead for two additional leads. Yet another neurostimulator may drive twelve electrodes per lead for two leads.

In these variations, entirely different header designs are used. Such header designs conventionally use ribbon bonds and lead frames as the interconnection between the feedthrough and the pressure contact, often a canted-coil spring, in the header. The development and resulting design for the ribbon bonds, lead frames, and related feedthrough become very specific for each IMD model and related leads and does not directly transfer to other IMD models and leads. Furthermore, the manufacturing processes to construct the headers having distinct designs for the different IMD models can be challenging. Thus, the development and manufacturing processes for headers being designed for each of the IMD models is burdensome.

In addition to the burdens of development and manufacturing, the designs that involve a relatively large number of pressure contacts in the header per lead can be troublesome. Typically, the pressure contacts such as the canted-coil springs can necessitate a large insertion force when numerous pressure contacts are needed for a particular lead. The insertion force may exceed the capabilities of the lead to maintain physical integrity. Lead insertion may be difficult and lead damage may also occur during insertion.

Furthermore, the size of the header is directly related to the connector spacing on the lead, or lead pitch. As the number of electrodes per lead increases the header size increases, and the increase may be significant due to the relatively large size of conventional electrical contacts such as the canted-coil springs. This relationship contradicts the efforts to develop smaller IMDs which are often more desirable for implantation.

SUMMARY

Embodiments address issues such as these and others by providing various features for headers installed on an IMD. For instance, in some embodiments, headers may be constructed of individual modules that may be stacked together to form a passageway for the lead within the header. The modules may have a particular design for a lead passageway that is replicated from one header design to the next to produce the desired number of lead passageways for a particular IMD and therapy. Electrical contacts may be provided between various modules so that the number and placement of the electrical contacts may be more easily selected and varied from one header design to the next.

In some embodiments, the electrical contacts of the header may have a design that allows several modules to be stacked while retaining a relatively small contact spacing known as pitch and while retaining a relatively small insertion force requirement. The electrical contacts may be in the form of a contact conductor that surrounds the lead passageway while having a relatively small thickness in the axial dimension of the lead passageway, such as on the order of 0.040 inches or less. The electrical contact may include multiple radial protrusions spaced about the contact. These radial protrusions may engage the electrical connectors on a lead being inserted into the lead passageway of the header.

Furthermore, in some embodiments, the electrical contacts may float within the lead passageway of the header. The ability to float with subtle radial movements during insertion better aligns the contact to the lead connectors. As the proximal end of the lead and the series of lead connectors on the proximal end may have concentricity imperfections, the floating electrical contact further lessens insertion force requirements.

In some embodiments, the feedthrough of the IMD may provide a direct connection to the electrical contact in the lead passageway of the header to avoid intervening conductors and related connections. The feedthrough pins may exit the IMD housing and then extend through a channel of the header to contact extensions of the electrical contacts present within the header. The header may further be encapsulated in a polymer to isolate the conductors present within the channels from the body tissue.

DETAILED DESCRIPTION

Embodiments provide for implantable medical devices having headers that allow for device and lead configuration variants. Embodiments of the headers may be modular whereby contact modules of a particular design may be stacked to achieve the number of electrical contacts that are necessary for a given device and lead configuration.

Embodiments of the headers may simplify connectivity to the device by providing for direct electrical connections between the electrical contacts of the header and the feedthrough pins of the device. The feedthrough pins may pass through channels within the header to achieve electrical connection to the electrical contacts of the header.

Embodiments of the headers may allow for a relatively large number of electrical connections for a given lead by providing relatively thin electrical contacts, on the order of 0.040 inches or less in the axial dimension. The thin nature of the electrical contacts reduces the axial space needed for a large number of electrical connections to a lead.

Embodiments of the headers may allow for a relatively large number of electrical connections for a given lead by reducing scraping forces that occur during lead insertion. The reduction may be provided by the thin and flexible nature of radial protrusions of some embodiments of the electrical contacts within the header. The reduction may be additionally or alternatively provided by allowing the electrical contact to radially float within the header to better align with concentricity variations of the lead.

Figure 1:
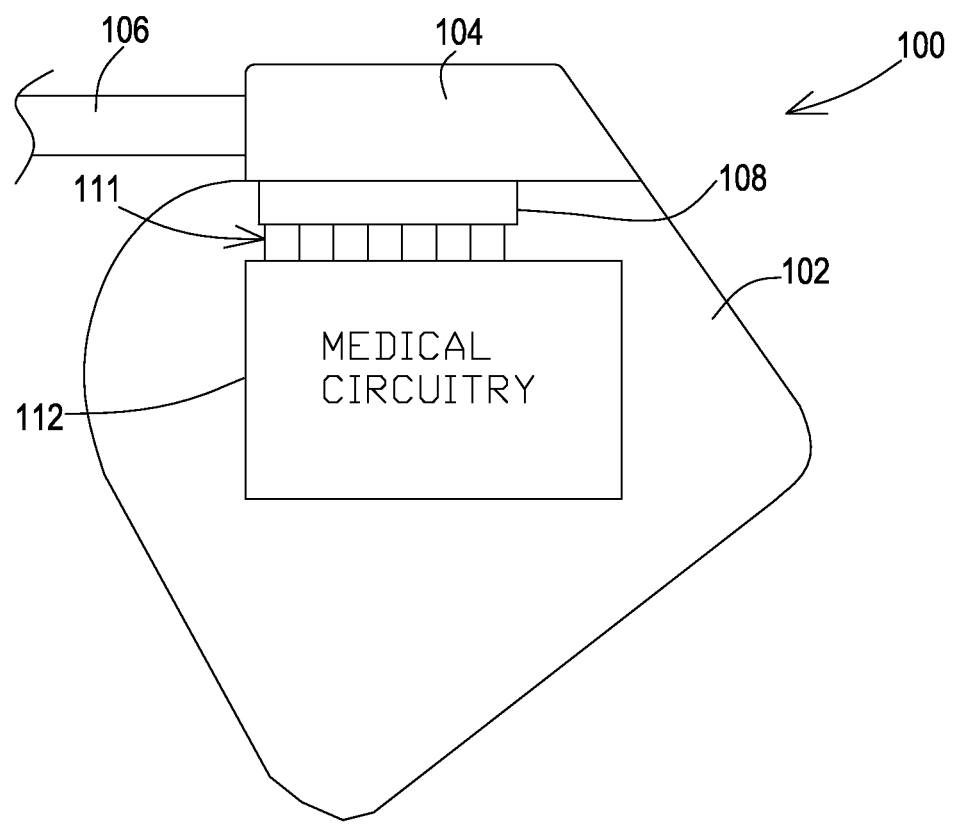
FIG. 1 shows an implantable medical device including an embodiment of a header.

FIG. 1 shows one example of an implantable medical device (IMD) 100. The IMD 100 includes a housing 102 that encloses medical circuitry 112 that is used to provide the medical function of the IMD 100. The medical circuitry 112 may include various components such as one or more batteries, controllers, pulse generators, and the like. The housing 102 is typically constructed of biocompatible materials such as various grades of titanium. The IMD 100 is typically implanted at a site within a patient's body or may be mounted externally of the body in some instances.

The IMD 100 includes a feedthrough 108 that provides a passageway for electrical pins 111 that exit the medical circuitry 112. The electrical pins 111 pass through the feedthrough 108 to exit the housing 102.

The IMD 100 also includes a header 104 that is mounted to the housing 102 in a sealed relationship that resists body fluids from penetrating into the junction to the housing 102. The header 104 receives the electrical pins 111 exiting the housing 102 via the feedthrough 108. The header 104 includes one or more lead passageways that each receives a proximal end of a medical lead 106. The header 104 may include various structures for fixing the medical lead 106, such as set screw blocks and the like. The set screw block or other manner of fixing the lead 106 may be located within a contact module or the header 104, for instance the most distal contact module. The medical lead 106 that is inserted into the header 104 has electrical connectors on the proximal end, electrodes on a distal end, and conductors that interconnect the two.

The header 104 includes electrical contacts, discussed in more detail below, that contact corresponding electrical connections of the medical lead 106. These electrical contacts are also in electrical communication with corresponding electrical pins 111 and carry electrical signals between the electrical connections of the lead 106 and the electrical pins 111 of the medical circuitry 112.

Figure 2:
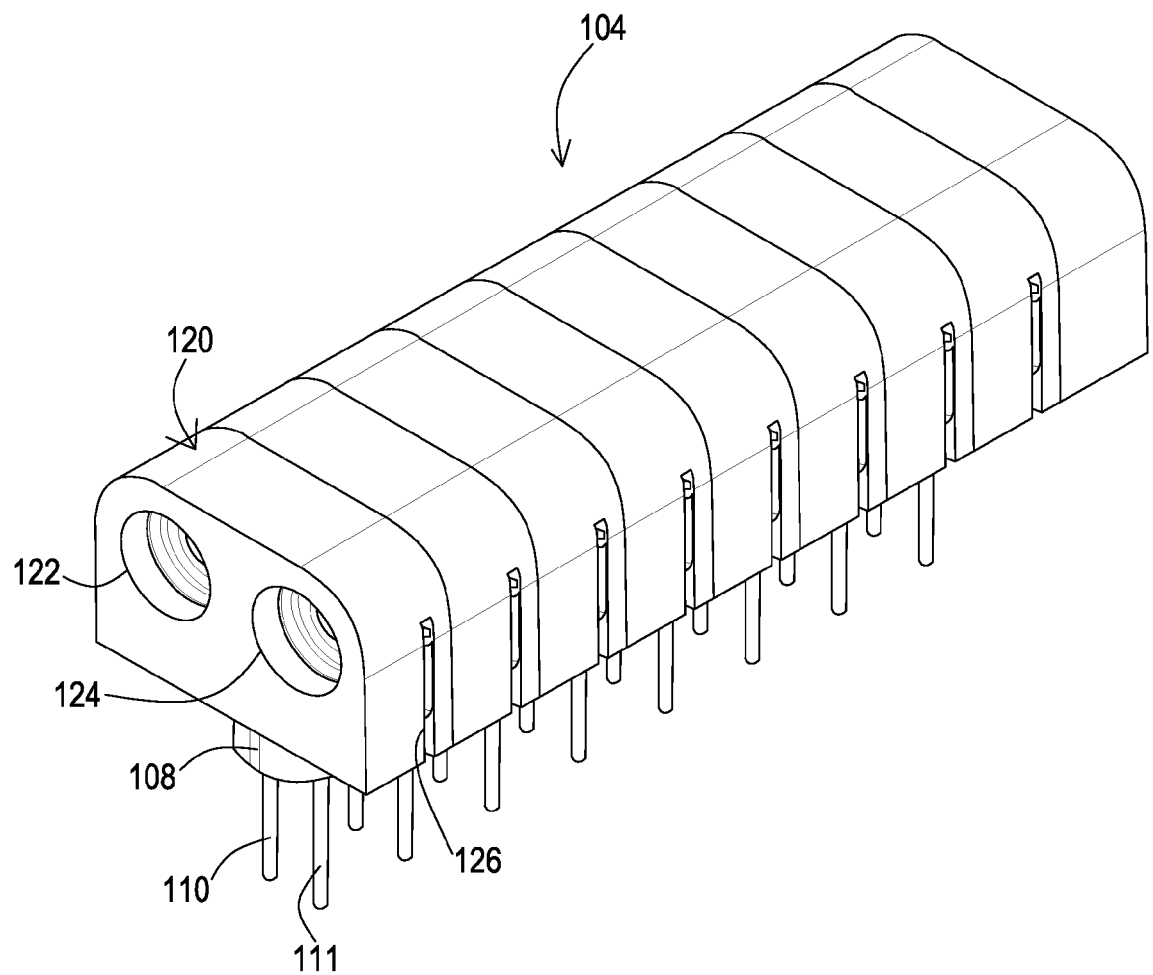
FIG. 2 shows a perspective view of an embodiment of the header and a feedthrough of the implantable medical device.

FIG. 2 provides a view of the internal components of one embodiment of the header 104. These components include a series of contact modules 120 that are stacked to create the axial dimension of the header 104. It should be noted that the contact modules 120 being stacked refers to being positioned immediately adjacently to one another without regard to horizontal or vertical orientation of the stack. The contact modules 120 may be constructed of various non-conductive materials that ultimately provide a rigid structure such as injection molded plastics. The contact modules 120 house other components such as the electrical contacts of the header 104. Once these components are installed relative to the contact modules 120, the contact modules 120 may be stacked together in the length needed for a particular device and lead configuration. The contact modules 120 may also then be fused by a process such as an ultrasonic weld or adhesive bonding to create one rigid and sealed header body. The stacking and sealing may be done by holding each module relative to a common reference point to improve the dimensional tolerance of the final assembly.

FIG. 2 also shows the feedthrough 108 and two sets of electrical feedthrough pins 110, 111 that correspond to two lead passageways 122, 124, respectively, of each contact module 120 and ultimately the header 104. As can be seen in FIG. 2 and also in FIG. 5, each contact module 120 includes a channel 126 that receives the corresponding feedthrough pin 111. In this dual passageway embodiment, the opposite side of each contact module 120, as seen in FIG. 4, also includes a channel 136 that receives the corresponding feedthrough pin 110. FIG. 4 is discussed in more detail below. It will be appreciated that embodiments may include any number of lead passageways including horizontally and/or vertically spaced passageways within a given header 104.

While the contact modules 120 are visible in FIG. 2, the series of contact modules 120 forming the header 104 may be encapsulated in a polymer shell. This may be beneficial for embodiments where the channels 126, 136 are otherwise exposed. The polymer shell may seal the channels 126, 136 so that the feedthrough pins 110, 111 are not exposed to ambient conditions about the header 104, which prevents conductive bodily fluids from short circuiting the feedthrough pins 110, 111. As an alternative to, or in addition to the polymer shell, the feedthrough pins 110, 111 may be coated with a non-conductive material, such as polytetrafluoroethylene (PTFE) or ethylene tetrafluoroethylene (ETFE) to prevent short circuiting between feedthrough pins 110, 111.

Figure 3:
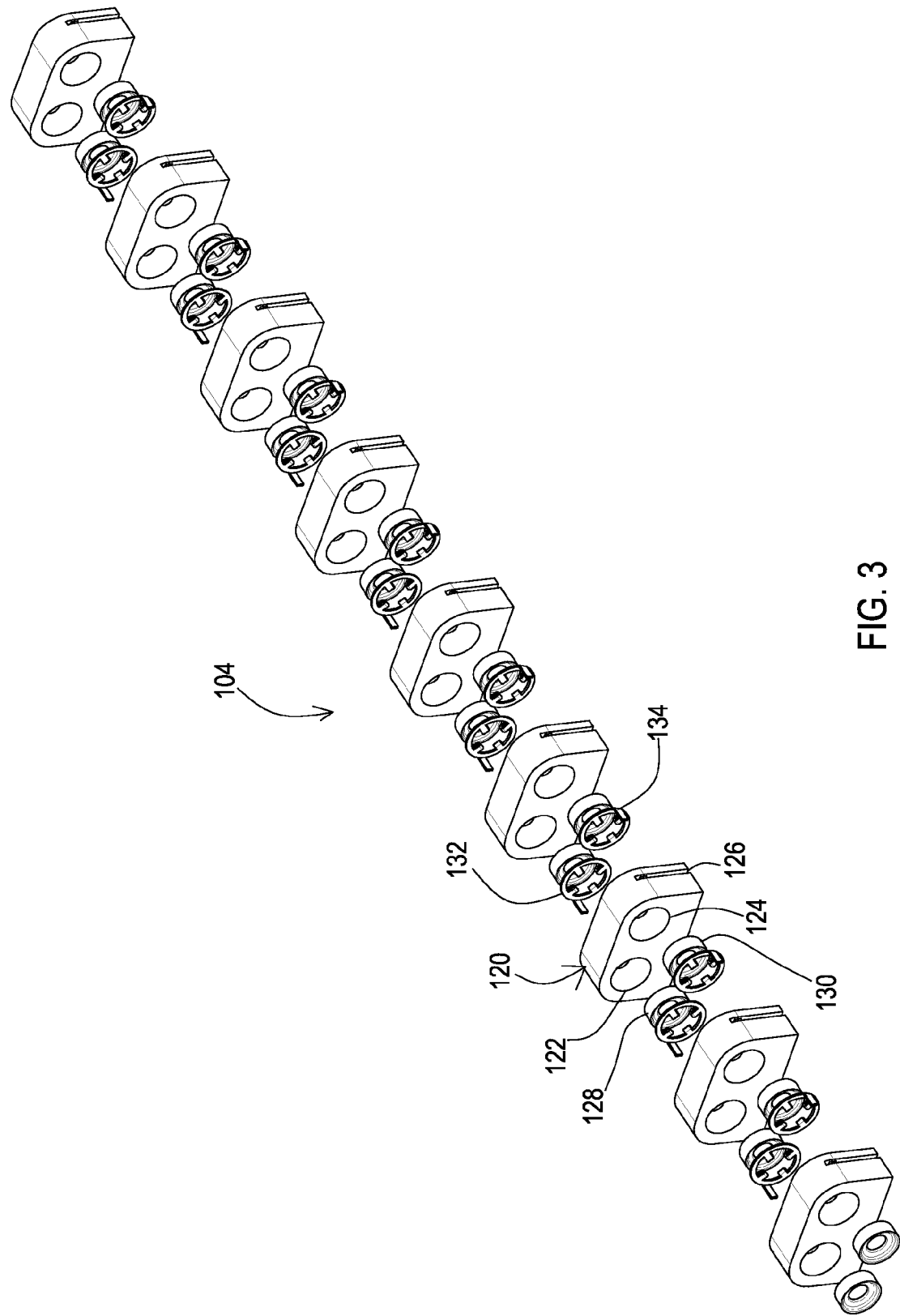
FIG. 3 shows an exploded perspective view of contact modules of an embodiment of the header.

FIG. 3 shows an exploded view of the header 104 and each of the components of this particular embodiment. Each lead passageway 122, 124 of each contact module 120 receives a corresponding contact isolator 128, 130, respectively. Each lead passageway 122, 124 of each contact module 120 also receives a corresponding electrical contact 132, 134, respectively. The contact isolator 128, 130 is present to provide a sealing engagement to the insulator of the lead body that is present between electrical connectors of the lead 106. This sealing engagement provides a degree of isolation between the series of electrical contacts 132, 134 of the header 104 so that the distinct electrical pathways are less likely to become electrically shorted by conductive bodily fluids that are present about the header 104.

Figure 4A:
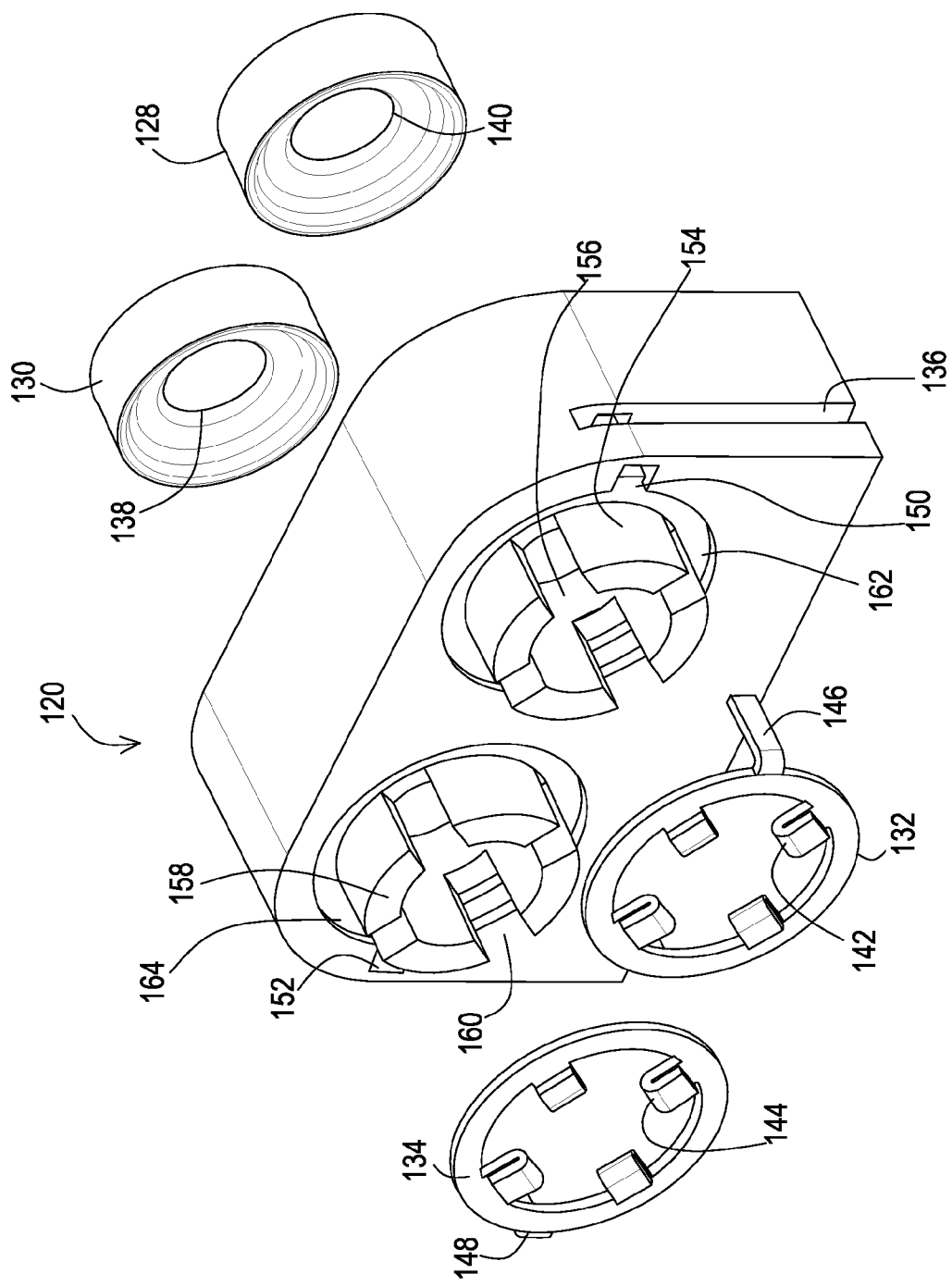
FIG. 4A shows an exploded perspective view of a contact module, electrical contact, and contact isolator of an embodiment of the header.

FIG. 4A shows the contact module 120, contact isolators 128, 130, and electrical contacts 132, 134 according to this particular embodiment from the opposite side of that shown in FIG. 3. The contact module 120 has a set of axial extensions 154, 158 that upon assembly enter the lead passageway 122, 124 of the adjacent contact module 120. This engagement of the axial extensions 154, 158 to the lead passageways 122, 124 aids in properly aligning the contact modules 120 and also provides structural support for the header structure 104 by stabilizing the position of one contact module 120 relative to an adjacent one both before and after fusing of the contact modules 120.

In this embodiment, the contact module 120 may have various features that relate to the electrical contacts 132, 134. The axial extensions 154, 158 are arranged circumferentially and define spaces 156, 160 that accommodate the electrical contacts 132, 134. The electrical contacts 132, 134 of this embodiment are thin conductive rings with radial protrusions 142, 144. These radial protrusions 142, 144 reside within the spaces 156, 160 as the electrical contacts 132, 134 are placed about the axial extensions 154, 158. The contact module 120 may include recesses 162, 164 that allow the electrical contacts 132, 134 to rest in place between adjacent contact modules. The contact module 120 may also include axial channels 150, 152 that intersect with the feedthrough pin channels 136, 126, respectively, and that receive axial extensions 146, 148 of the electrical contacts.

The electrical contacts 132, 134 of this particular embodiment utilize the radial protrusions 142, 144 to establish physical and electrical contact with the electrical connectors of the leads 106. In the example shown, there are four radial protrusions, each having a U shape with the bend of the U shape providing the contact surface. This relatively small point of contact may be useful to lessen the scraping force that occurs during lead insertion. Furthermore, the radial protrusions may be provided with a degree of flexibility so that they may deflect slightly in the axial direction to further reduce scraping forces and to snugly engage the electrical connectors of the leads 106.

An additional feature of the electrical contacts 132, 134 relevant to lead insertion may be a radial floating relationship to the contact module 120. This radial floating relationship may be provided by having electrical contacts 132, 134 with an inner diameter that is greater than the outer diameter established by the axial protrusions 154, 158. An outer diameter of the electrical contacts 132, 134 may be less than the outer diameter established by the recesses 162, 164. The spacing between axial extensions 154, 158 of a set may be greater than the width of the radial protrusions 142, 144. As a result of these size relationships, a degree of freedom in the radial direction is established for the electrical contacts 132, 134 that allows the electrical contacts 132, 134 to better accommodate concentricity imperfections in the leads 106 as they are being inserted.

The axial extensions 146, 148 of the electrical contacts 132, 134 pass through the channels 150, 152 to intersect the feedthrough pins 110, 111 present within the channels 136, 126. Electrical connectivity is established at this intersection by the physical contact of the feedthrough pins to the axial extensions 146, 148, and this physical contact may be secured by welding.

The electrical contacts 132, 134 may be constructed of various conductive materials such as titanium, titanium alloys, MP35N, and the like. The electrical contacts may be of various sizes; however, a thickness ranging from 0.004 to 0.040 inches may have adequate structural integrity while offering the benefit of reduced scraping force. For the electrical contact 132 as shown, the thickness may range from 0.004 to 0.020 inches so that the resulting thickness of the radial protrusion ranges from 0.008 to 0.040 inches. Furthermore, the thin nature of the electrical contact may allow for a relatively small center-to-center spacing of electrical contacts known as lead pitch, such as 0.080 inches or less.

While the electrical contacts 132, 134 of a particular design are shown relative to the contact module 120, it will be appreciated that other electrical contact designs are also applicable to a header constructed from a series of contact modules. Likewise, while a particular header design employing a series of contact modules is shown, it will be appreciated that other header designs including non-modular designs are also applicable for use of thin electrical contacts with radial protrusions.

Figure 4B:
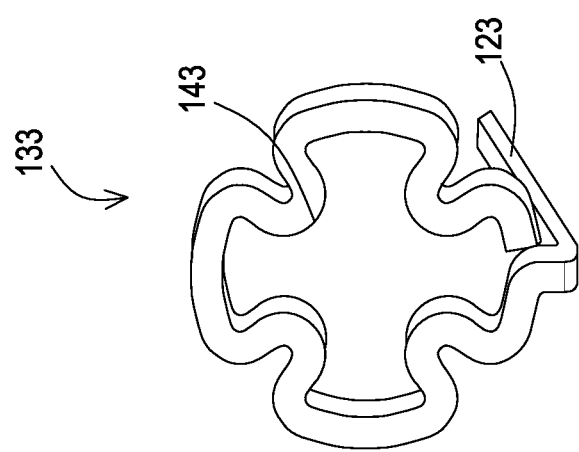
FIG. 4B shows an alternative electrical contact.

FIG. 4B shows an alternative electrical contact 133. This electrical contact 133 is a wireform that also is within and surrounds the lead passageway 122, 124 and is contained by axial extensions of a contact module. The axial extensions that cooperate with the electrical contact 133 are shaped to fit the particular wireform shape, as opposed to having the shape shown in FIG. 4A. The wireform electrical contact 133 may be sized to float in the same manner as the electrical contact of FIG. 4A. The wireform electrical contact 133 may also have a thickness in the axial direction on the order of 0.004 to 0.040 inches.

In this particular example, the wireform electrical contact 133 is in the shape of a shamrock and includes four radial protrusions 143 to establish points of contact on the electrical connector of the lead 110. However, it will be appreciated that other wireform shapes are applicable such as a triangular shape, diamond shape, and the like where small points of contact to the lead connector are established by the linear regions of the shape rather than by radial protrusions. The wireform electrical contact 133 also includes an extension 123 that may extend along the channels 150, 152 to reach the feedthrough pins 110, 111.

FIG. 4A also shows the contact isolators 128, 130 which are positioned within the lead passageways 122, 124 to form a seal at the point of contact with the contact modules 120. These contact isolators include apertures 140, 138 through which the leads 106 pass during insertion into the header 104. The apertures 140, 138 may have a diameter that is slightly less than that of the leads 106. Furthermore, the contact isolators 128, 130 may be constructed of an elastic material such as silicone rubber so that the aperture expands during lead insertion and forms a tight seal against the lead body to reduce the likelihood of bodily fluids creating a conductive path from one electrical contact of one contact module to an electrical contact of an adjacent module.

The contact isolators 128, 130 are elastic while the contact modules 120 are rigid and thus the two types of components may be manufactured separately as shown. However, a co-injection molding process may instead be used to form the contact isolators 128, 130 from an elastic material together with the contact module 120 from a rigid material together as one piece.

Figure 5:
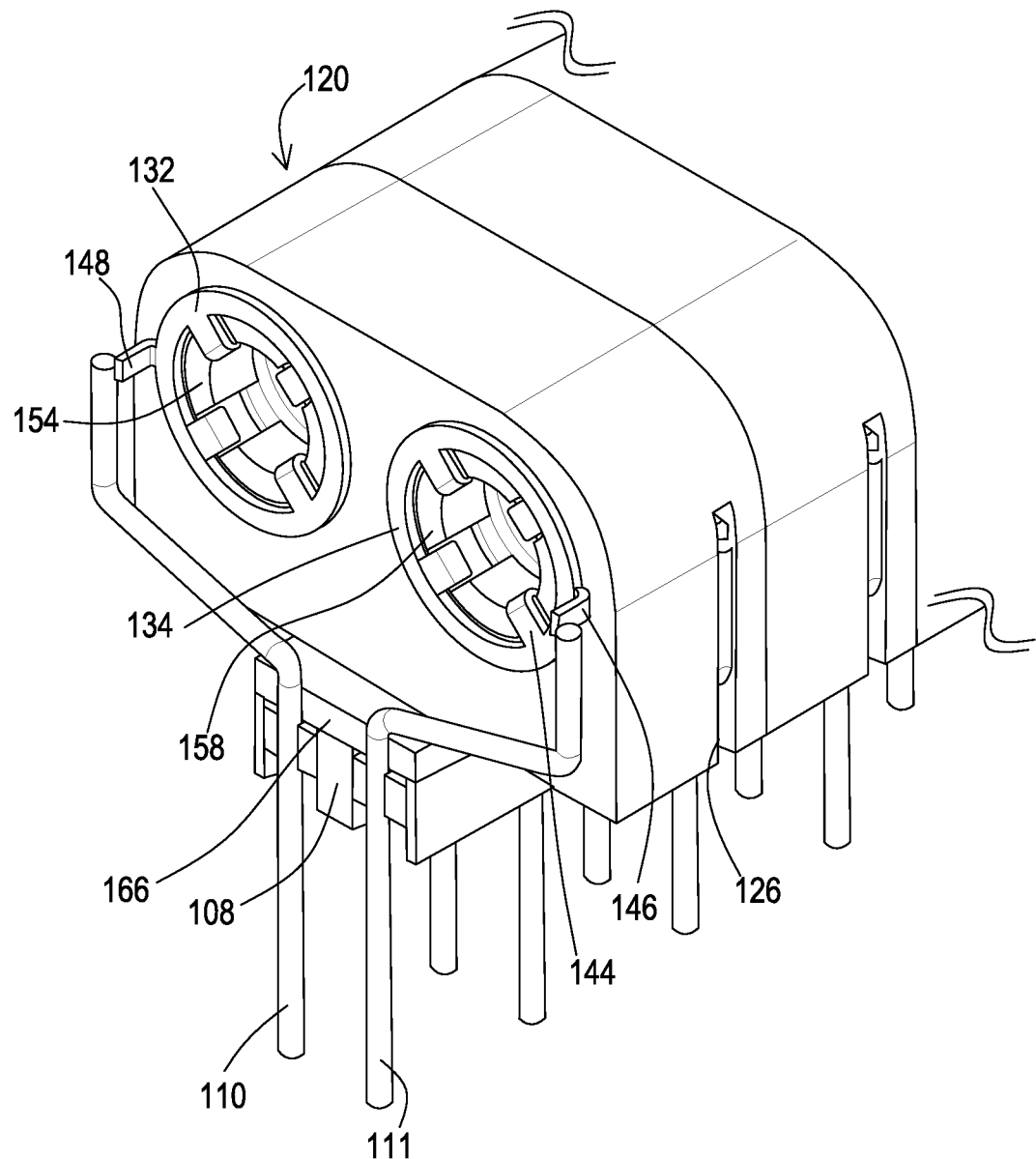
FIG. 5 shows a perspective view of a contact module with the connection of feedthrough pins to electrical contacts.

FIG. 5 shows the side of the contact module 120 opposite that of FIG. 4, with the electrical contacts 132, 134 in position. A contact module is partially omitted to reveal the intersection of the extensions 146, 148 and the feedthrough pins 111, 110 which achieve electrical connectivity as discussed above in relation to FIG. 4A. The partially omitted contact module's axial extensions 154, 158 are visible in FIG. 5 within the adjacent contact module.

FIG. 5 also reveals a cross-section of the feedthrough 108 and a pin isolator 166 that resides between the feedthrough 108 and the bottom of the series of contact modules 120. The pin isolator 166 is constructed of an elastic material, such as silicone rubber, that provides isolation by compression sealing. This isolates the feedthrough pins 110, 111 from each other as well as from the outside environment.

Figure 6:
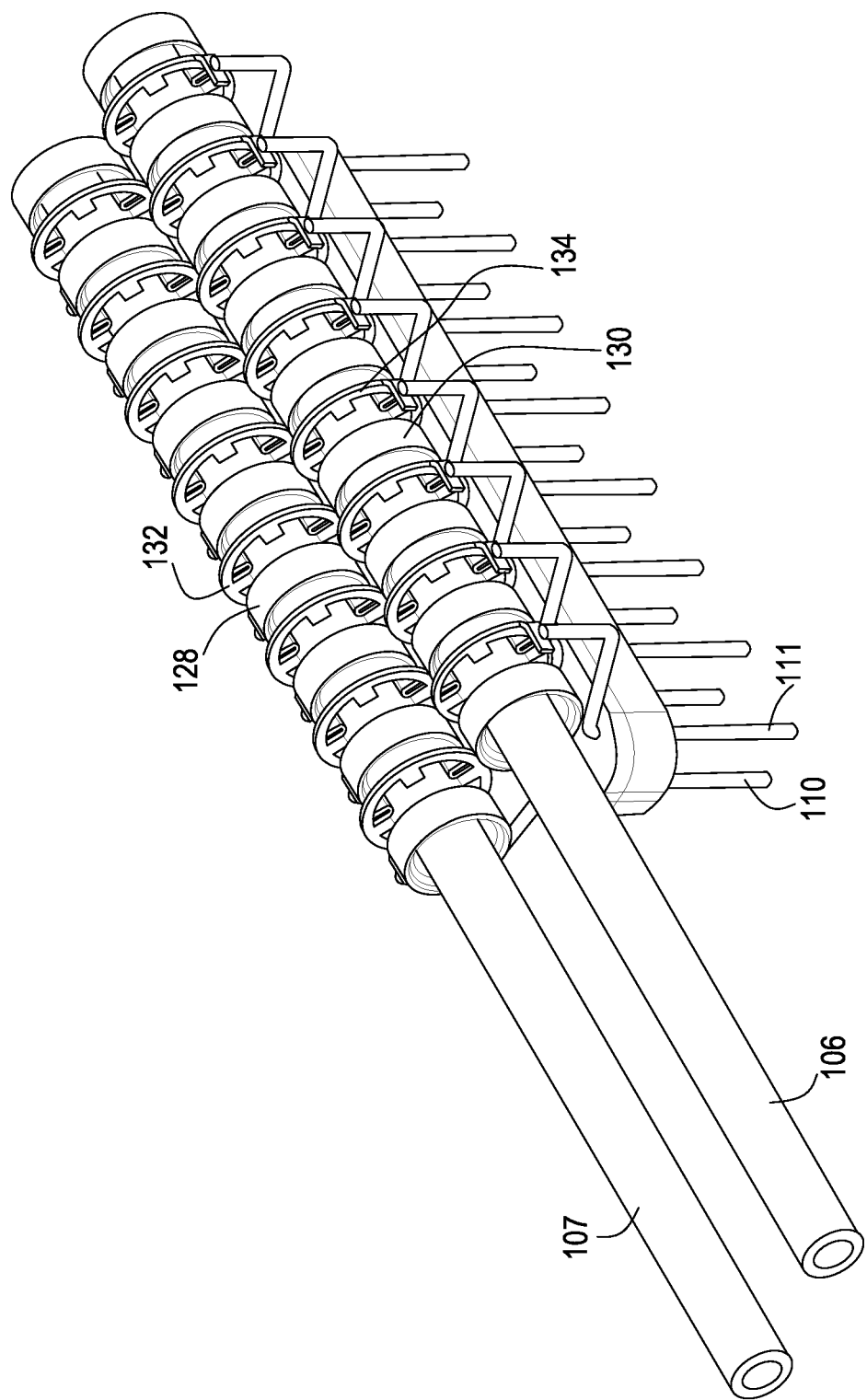
FIG. 6 shows a perspective view of an arrangement of feedthrough pins, electrical contacts, and contact isolators with the contact modules being omitted for clarity.

FIG. 6 shows a view of the header components installed over the feedthrough 108 and pin isolator 166 but with the contact modules omitted for clarity of illustration. In this view, both leads 106, 107 can be seen entering the respective lead passageways provided by the positioning of the electrical contacts 132, 134 and contact isolators 128, 130. This view also illustrates the relative placement of the electrical contacts and contact isolators where it can be seen that each electrical contact 132, 134 is axially between a pair of axially spaced contact isolators 128, 130 on each side to provide a sealed space for each electrical contact 132, 134.

Figure 7:
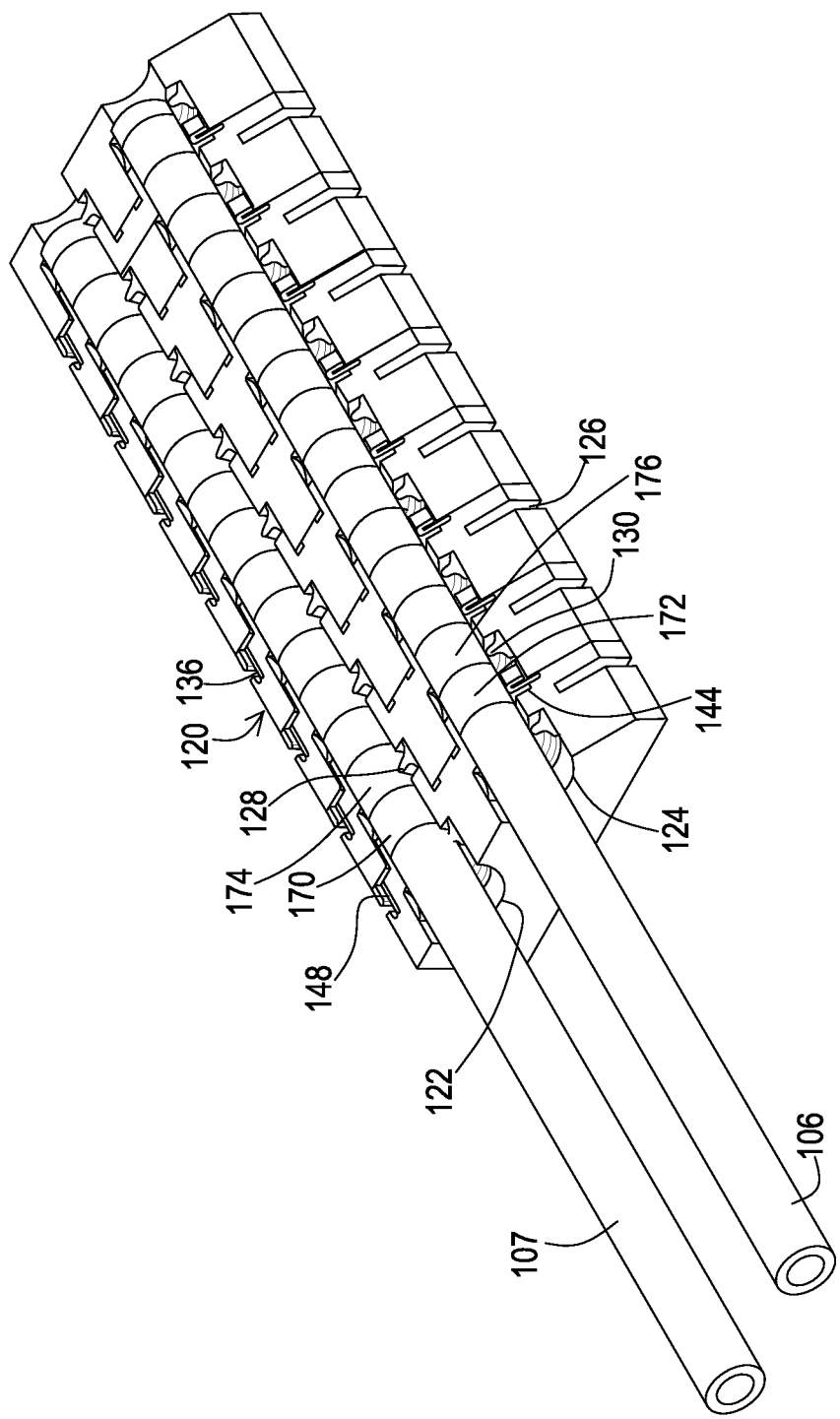
FIG. 7 shows a perspective cross-sectional view taken through two separate planes of an embodiment of a header and corresponding medical leads.

FIG. 7 shows a cross-sectional perspective view of this example of a header 104 with the leads 106, 107 in their inserted position. There are two cross-sectional cuts through the embodiment shown in FIG. 2 that are visible in this view. A first cut is taken through the center of the lead passageway 122 in a plane that also intersects the center of the lead passageway 124. The second cut is taken through the center of the lead passageway 124 at approximately a 45 degree angle relative to the first cut. The first and second cuts allow for different details to be exposed within the header 104 for the two lead passageways and in relation to electrical connectors 170, 172 of the leads 106 and 107.

Figure 8:
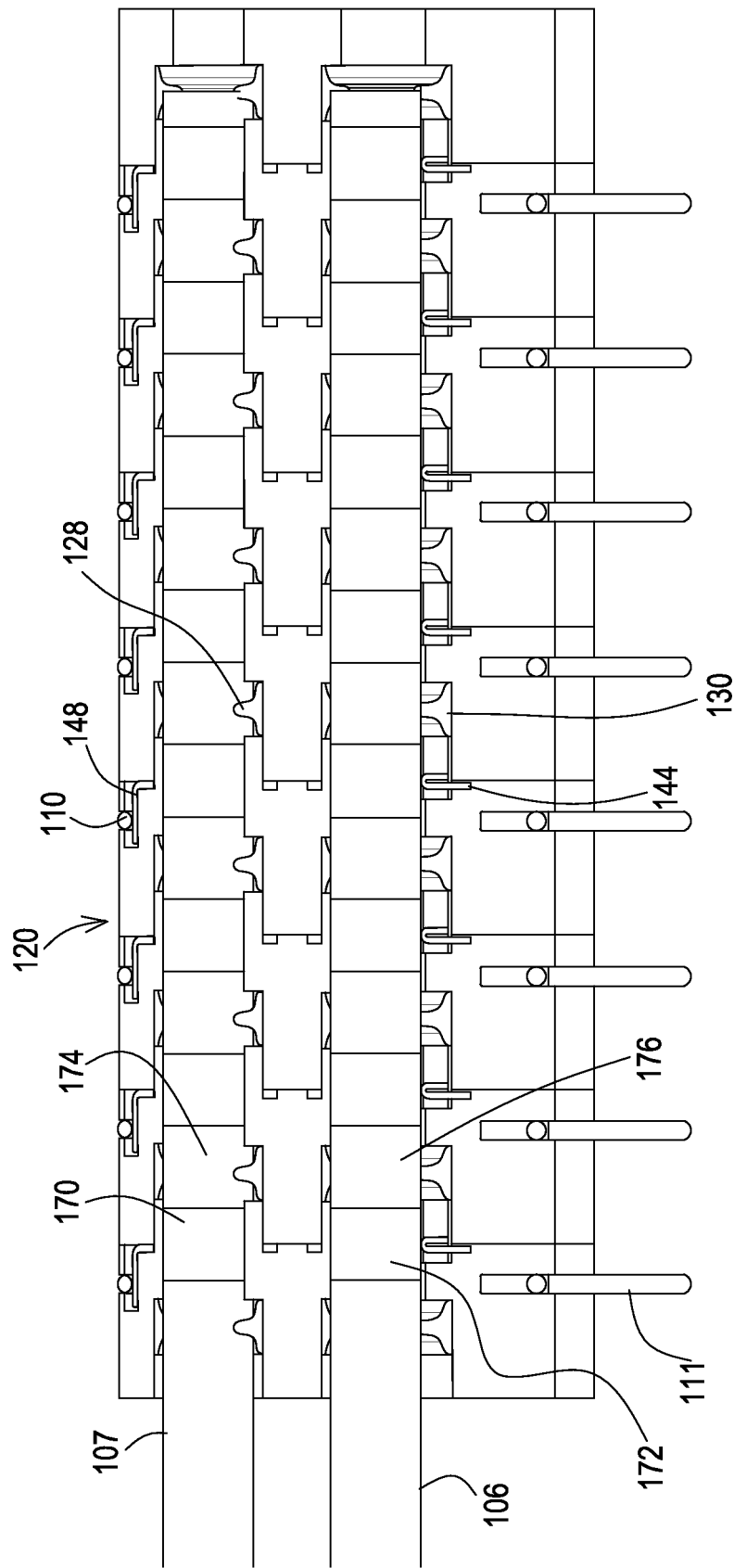
FIG. 8 shows a top view normal to one plane of the cross-section of FIG. 7.
Figure 9:
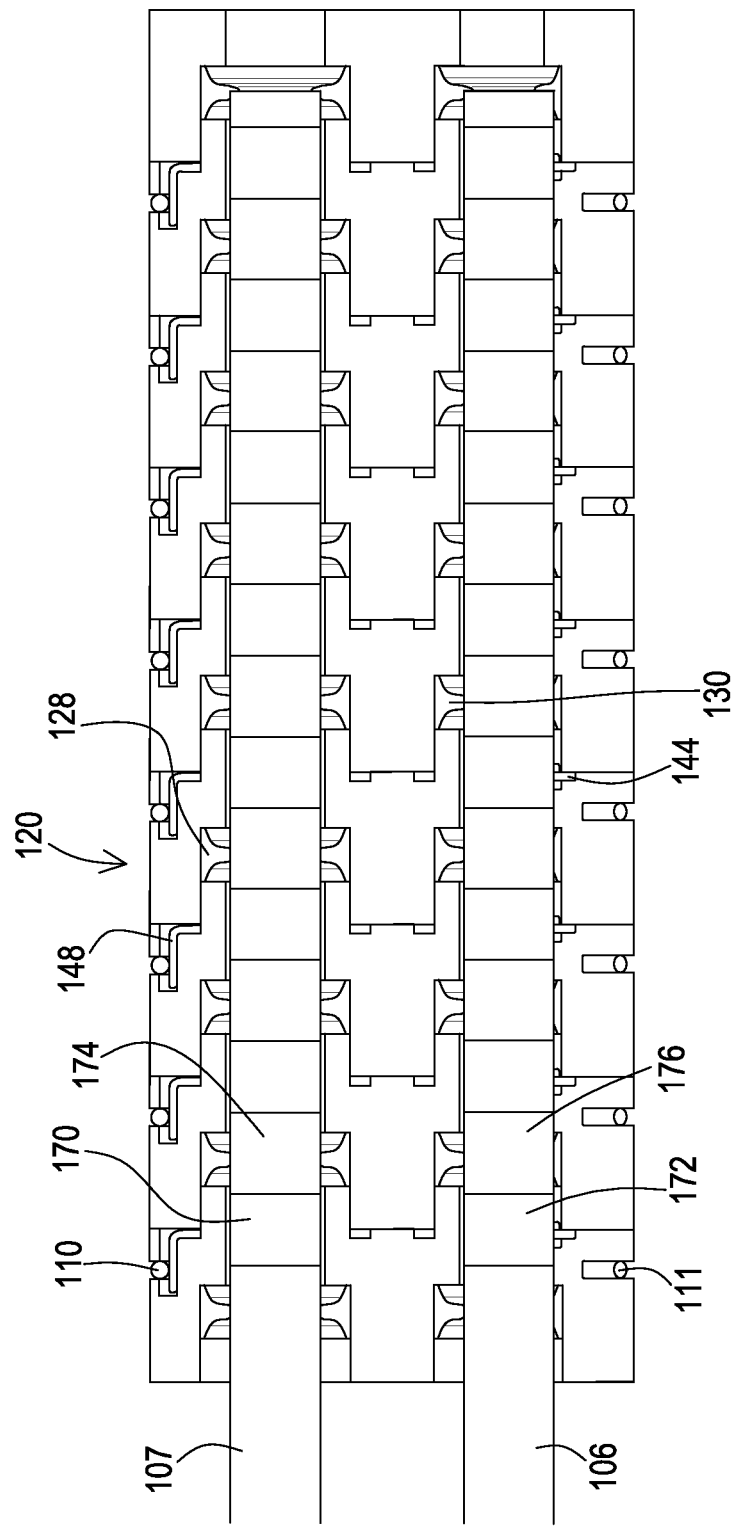
FIG. 9 shows a top view normal to another plane of the cross-section of FIG. 7.

FIG. 7 provides a reference for viewing FIGS. 8 and 9. FIG. 8 is a top view of the header 104 from the perspective that is normal to the plane of the second cut of FIG. 7. FIG. 9 is a top view of the header 104 from the perspective that is normal to the plane of the first cut of FIG. 7. The feedthrough pins 110, 111 are omitted from FIG. 7 but are present and visible in FIGS. 8 and 9.

FIGS. 7-9 show electrical connectors 170, 172 of the leads 107, 106, respectively. FIGS. 7-9 also show the insulator sections 174, 176 of the leads 107, 106, respectively, that are positioned between electrical connectors. FIGS. 7-9 also show the containment of the electrical contacts 132, 134 and contact isolators 128, 130 within the contact modules 120. It can be seen that the contact isolators 128, 130 are positioned between an end of the axial extensions of one contact module and an inner abutment of an adjacent contact module.

FIGS. 7 and 8 most clearly show the presence of the radial protrusions 144 of the electrical contacts 134 making physical and electrical connection to the electrical connectors 172 of the lead 106. The radial protrusions 142 of the opposite lead passageway make the same physical and electrical connection of the electrical connectors 170 but are not visible in these particular cross-sectional views. In this particular example, as shown in FIG. 4, the radial protrusions 142, 144 and the spaces 156, 160 defined by the axial protrusions 154, 158 are at approximately 45 degree angles relative to the plane passing through the center of both lead passageways 122, 124. Thus, the 45 degree cut for the lead passageway 124 in FIGS. 7 and 8 reveals the radial protrusions 144 of this particular example. It will be appreciated that the radial protrusions 142, 144 may be at other angles as may the spacing from the axial extensions for those embodiments that include axial extensions.

FIGS. 7 and 9 most clearly show the presence of the contact isolators 128 within the lead passageway 122 making physical contact with the insulator sections 174 of the lead 107. As discussed above, this contact establishes a seal on each side of each electrical contact to electrical connector pairing to reduce the likelihood of fluid conducting between adjacent electrical contacts. The contact isolators 130 of the opposite lead passageway 124 make the same contact with the insulator sections 176 of the lead 106, but the contact is not as clearly viewable in these figures due to the 45 degree cut through the lead passageway 124.

FIGS. 8 and 9 also show the intersection and resulting contact of the conductive extension 148 of each electrical contact 132 to the feedthrough pin 110 present within the channel 136. This contact establishes electrical continuity from the feedthrough pin 110 to the electrical contact 132, and ultimately from the medical circuit 112 to an electrode (not shown) at the distal end of the lead 107. The conductive extension 146 of each electrical contact 134 establishes the same contact to the feedthrough pins 111 present within the channel 126, but that intersection is not visible in these views due to the 45 degree cut through the lead passageway 124.

Various features of the illustrative embodiments are applicable in other embodiments independently of other features disclosed herein. For instance, the modular construction of the header may be achieved by using contact modules but while not necessarily using other features. As one example, the modular header may be constructed of contact modules that accommodate a conventional intervening lead frame connection between the feedthrough and the electrical contacts. As another example, the modular header may be constructed of contact modules that accommodate conventional canted spring connectors that may or may not float.

The direct connection of feedthrough pins to electrical contacts may be achieved while not necessarily using other features. As one example, the direct connection of feed through pins and electrical contacts may be present for a non-modular header construction that accepts feedthrough pins via a channel that extends to the electrical contacts. As another example, the direct connection of feedthrough pins and electrical contacts may be present for an electrical contact that is mounted within the header in a fixed, non-floating manner.

The relatively thin electrical contacts with or without radial protrusions may be used while not necessarily using other features. As one example, these electrical contacts may be present within a non-modular header construction that accepts these electrical contacts in a fixed or floating manner. As another example, these electrical contacts may be present where an intervening lead frame connects the feedthrough pins to the electrical contacts.

Furthermore, the floating nature of the electrical contacts may be used while not necessarily using other features. For example, an electrical contact may float within a non-modular header construction where the recessed area where the electrical contact is present provides freedom of movement in a radial direction. As another example, an electrical contact may float where an intervening lead frame connects the feedthrough pins to the electrical contact. As another example, an electrical contact may float within a header while having a different design than being relatively thin with radial protrusions.

Embodiments provide for an implantable medical device that includes a housing, circuitry within the housing, and a feedthrough electrically connected to the circuitry and providing pins externally of the housing. A header is mounted to the housing and includes a plurality of adjacent contact modules, each contact module having at least one lead passageway. A plurality of contact isolators are included in the header, with a contact isolator of the plurality being disposed within each of the at least one lead passageways of the corresponding contact modules of the plurality. A plurality of electrical contacts are positioned within the lead passageway, with at least one electrical contact of the plurality being located axially between contact isolators, each of the plurality of contacts being in electrical communication with a corresponding pin of the feedthrough.

Each contact module may have axial extensions spaced circumferentially on a first end, the plurality of contact modules being stacked so that an axial extension of one contact module fits into the lead passageway of an adjacent contact module. Each contact isolator of the plurality may be present between an abutment within the at least one lead passageway of the corresponding contact module and an end of the axial extensions of an adjacent contact module that are present within the at least one lead passageway of the corresponding contact module. Each electrical contact of the plurality may be disposed about the axial extensions of the plurality of contact modules.

Each of the electrical contacts may include an extension that is present within a first channel of the contact modules, and each pin of the feedthrough may be present within a second channel of the contact modules to contact a corresponding extension of the electrical contacts. The header may be encapsulated in a polymer. Each of the electrical contacts may surround the lead passageway and include flexible radial protrusions. The plurality of adjacent contact modules may be fused. At least one contact isolator of the plurality may be co-molded with a corresponding contact module. Each contact isolator may be made of a material such as silicone rubber.

Embodiments provide for an implantable medical device that includes a housing, circuitry within the housing, and a feedthrough electrically connected to the circuitry and providing pins externally of the housing. A header is mounted to the housing, the header defining at least one lead passageway and comprising a plurality of electrical contacts. Each of the electrical contacts includes an extension that is present within the header, with each pin of the feedthrough extending through one channel of a set of channels of the header to contact a corresponding extension of the electrical contacts.

The header of this implantable medical device embodiment further may include a plurality of adjacent contact modules, with each contact module having at least one lead passageway. A plurality of contact isolators may be included within the header, with a contact isolator of the plurality being disposed within each of the at least one lead passageways of the corresponding contact modules of the plurality. The plurality of electrical contacts may be positioned within the at least one lead passageway, with at least one electrical contact being located axially between contact isolators.

Each contact module of this implantable medical device embodiment may have axial extensions spaced circumferentially on a first end, the plurality of contact modules being stacked so that an axial extension of one contact module fits into the lead passageway of an adjacent contact module. Each contact isolator of the plurality may be present between an abutment within the at least one lead passageway of the corresponding contact module and an end of the axial extensions of an adjacent contact module that are present within the at least one lead passageway of the corresponding contact module. Electrical contacts of the plurality may be disposed about the axial extensions of the plurality of contact modules.

Each of the electrical contacts of this implantable medical device embodiment may surround the lead passageway and include flexible radial protrusions. The plurality of adjacent contact modules may be fused. Each contact isolator may be a ring. The header may be encapsulated in a polymer.

Embodiments provide an implantable medical device that includes a housing, circuitry within the housing, and a feedthrough electrically connected to the circuitry and providing pins externally of the housing. A header is mounted to the housing, the header defining at least one lead passageway and comprising a plurality of electrical contacts with each of the electrical contacts being electrically coupled to at least one pin. Each of the plurality of electrical contacts surrounds the lead passageway and has a thickness in an axial direction of 0.040 inches or less.

The electrical contact of this implantable medical device embodiment may float radially relative to the at least one lead passageway. The header may further include a plurality of adjacent contact modules, each contact module having at least one lead passageway. A plurality of contact isolators may be included within the header, with a contact isolator of the plurality being disposed within each of the at least one lead passageways of the corresponding contact modules of the plurality. The plurality of electrical contacts may be positioned within the at least one lead passageway of the adjacent contact modules, with at least one electrical contact being located axially between contact isolators.

Each contact module of this implantable medical device embodiment may have axial extensions spaced circumferentially on a first end, the plurality of contact modules being stacked so that an axial extension of one contact module fits into the lead passageway of an adjacent contact module. Each contact isolator of the plurality may be present between an abutment within the at least one lead passageway of the corresponding contact module and an end of the axial extensions of an adjacent contact module that are present within the at least one lead passageway of the corresponding contact module. Each electrical contact of the plurality may be disposed about the axial extensions of the plurality of contact modules.

Each of the electrical contacts of this implantable medical device embodiment may include an extension that is present externally of the contact modules, and each pin of the feedthrough may extend through channels of the contact modules to contact a corresponding extension of the electrical contacts. The header may be encapsulated in a polymer. Each of the electrical contacts may include flexible radial protrusions. The plurality of adjacent contact modules may be fused. Each contact isolator may be a ring. Each contact isolator may be made of a material such as silicone rubber.

Embodiments provide an implantable medical device that includes a housing, circuitry within the housing, and a feedthrough electrically connected to the circuitry and providing pins externally of the housing. A header is mounted to the housing, the header defining at least one lead passageway and comprising a plurality of electrical contacts with each of the electrical contacts being electrically coupled to at least one pin. Each of the plurality of electrical contacts being contained within the header while having a radially floating relationship to the lead passageway.

The header of this implantable medical device embodiment may further include a plurality of adjacent contact modules, each contact module having at least one lead passageway. A plurality of contact isolators may be included within the header, with a contact isolator of the plurality being disposed within each of the at least one lead passageways of the corresponding contact modules of the plurality. The plurality of electrical contacts may be positioned within the at least one lead passageway of the adjacent contact modules, with at least one electrical contact being located axially between contact isolators.

Each contact module may have axial extensions spaced circumferentially on a first end, the plurality of contact modules being stacked so that an axial extension of one contact module fits into the lead passageway of an adjacent contact module. Each contact isolator of the plurality may be present between an abutment within the at least one lead passageway of the corresponding contact module and an end of the axial extensions of an adjacent contact module that are present within the at least one lead passageway of the corresponding contact module. Each electrical contact of the plurality may be disposed about the axial extensions of the plurality of contact modules.

Each of the electrical contacts of this implantable medical device embodiment includes an extension that is present within a first channel of the contact modules, and wherein each pin of the feedthrough is present within a second channel of the contact modules to contact a corresponding extension of the electrical contacts. The header may be encapsulated in a polymer. Each of the electrical contacts may surround the lead passageway and comprises flexible radial protrusions. The plurality of adjacent contact modules may be fused. Each contact isolator may be a ring. Each contact isolator may be made of a material such as silicone rubber.

While embodiments have been particularly shown and described, it will be understood by those skilled in the art that various other changes in the form and details may be made therein without departing from the spirit and scope of the invention.

What is claimed is:

1. An implantable medical device, comprising:
    a housing;
    circuitry within the housing;
    a feedthrough electrically connected to the circuitry and providing pins externally of the housing; and
    a header mounted to the housing, the header defining at least one lead passageway in a longitudinal direction and comprising a plurality of electrical contacts, each of the electrical contacts defining an opening that is lateral to the longitudinal direction of the lead passageway and including a longitudinal extension that is present within one axial channel of a set of axial channels of the header that are separated from the lead passageway, with each pin of the feedthrough extending through one feedthrough channel of a set of feedthrough channels of the header that intersect with corresponding axial channels to contact a corresponding extension of the electrical contacts.

2. The implantable medical device of claim 1, wherein the header further comprises a plurality of adjacent contact modules, each contact module having module lead passageway such that the plurality of adjacent contact modules establish the at least one lead passageway of the header; and
    wherein each contact module has axial extensions, the plurality of contact modules being stacked so that an axial extension of one contact module fits into the lead passageway of an adjacent contact module.

3. The implantable medical device of claim 2, wherein the header further comprises:
    a plurality of contact isolators, with a contact isolator of the plurality of contact isolators being disposed within each of the at least one lead passageways of the corresponding contact modules of the plurality of contact modules; and
    wherein the plurality of electrical contacts are positioned within the at least one lead passageway, with each electrical contact being located axially between contact isolators.

4. The implantable medical device of claim 1, wherein each pin has a first section, a second section, and a third section, with a first bend joining the first and second section and a second bend joining the second and third section, wherein the first section exits from the feedthrough and wherein the third section contacts the axial extension.

5. An implantable medical device, comprising:
    a housing;
    circuitry within the housing;
    a feedthrough electrically connected to the circuitry and providing pins externally of the housing with each pin having a first section, a second section, and a third section, with a first bend joining the first and second section and a second bend joining the second and third section, wherein the first section exits from the feedthrough; and
    a header mounted to the housing, the header defining at least one lead passageway in a longitudinal direction and comprising a plurality of electrical contacts, with each pin of the feedthrough extending through one feedthrough channel of a set of feedthrough channels of the header to contact a corresponding electrical contact.

6. The implantable medical device of claim 5, wherein the header further comprises a plurality of adjacent contact modules, each contact module having module lead passageway such that the plurality of adjacent contact modules establish the at least one lead passageway of the header; and
    wherein each contact module has axial extensions, the plurality of contact modules being stacked so that an axial extension of one contact module fits into the lead passageway of an adjacent contact module.

7. The implantable medical device of claim 6, wherein the header further comprises:
    a plurality of contact isolators, with a contact isolator of the plurality of contact isolators being disposed within each of the at least one lead passageways of the corresponding contact modules of the plurality of contact modules; and
    wherein the plurality of electrical contacts are positioned within the at least one lead passageway, with each electrical contact being located axially between contact isolators.

8. A method of constructing an implantable medical device, comprising:
    providing a housing containing circuitry;
    mounting a feedthrough to the housing where the feedthrough has pins electrically connected to the circuitry where the pins extend from the feedthrough;
    constructing a header by:
        providing a plurality of adjacent contact modules, each contact module having at least one lead passageway;
        positioning a contact isolator of a plurality of contact isolators within each of the at least one lead passageways of the corresponding contact modules of the plurality of contact modules;
        positioning a plurality of electrical contacts within the lead passageway, with at least one electrical contact of the plurality of electrical contacts being located axially between contact isolators; and
        mounting the header to the housing and feedthrough such that each of the plurality of contacts is in electrical communication with a corresponding pin of the feedthrough.

9. The method of claim 8, wherein each contact module has axial extensions spaced circumferentially on a first end.

10. The method of claim 9, wherein the plurality of contact modules are stacked so that an axial extension of one contact module fits into the lead passageway of an adjacent contact module, wherein each contact isolator of the plurality of contact isolators is present between an abutment within the at least one lead passageway of the corresponding contact module and an end of the axial extensions of an adjacent contact module that are present within the at least one lead passageway of the corresponding contact module, and wherein each electrical contact of the plurality of electrical contacts is disposed about the axial extensions of the plurality of contact modules.

11. The method of claim 8, wherein each of the electrical contacts includes an extension that is present within a first channel of the contact modules, and wherein each pin of the feedthrough is present within a second channel of the contact modules to contact a corresponding extension of the electrical contacts.

12. The method of claim 8, further comprising encapsulating the header in a polymer.

13. The method of claim 8, wherein each of the electrical contacts surrounds the lead passageway and comprises flexible radial protrusions.

14. The method of claim 8, further comprising fusing the plurality of adjacent contact modules.

15. The method of claim 8, further comprising co-molding each of the plurality of contact isolators with a corresponding contact module.

16. The method of claim 8, wherein each contact isolator is made of silicone rubber.

\* \* \* \* \*